US010940048B2

(12) United States Patent
Locke

(10) Patent No.: US 10,940,048 B2
(45) Date of Patent: Mar. 9, 2021

(54) ASSEMBLY FEATURES AND METHODS FOR A PEEL-AND-PLACE DRESSING FOR USE WITH NEGATIVE-PRESSURE TREATMENT

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 175 days.

(21) Appl. No.: 15/997,763

(22) Filed: Jun. 5, 2018

(65) Prior Publication Data

US 2018/0353337 A1 Dec. 13, 2018

Related U.S. Application Data

(60) Provisional application No. 62/650,572, filed on Mar. 30, 2018, provisional application No. 62/633,438, (Continued)

(51) Int. Cl.
*A61F 13/00* (2006.01)
*A61F 13/02* (2006.01)
(Continued)

(52) U.S. Cl.
CPC ........ *A61F 13/00068* (2013.01); *A61B 46/20* (2016.02); *A61F 13/00059* (2013.01); (Continued)

(58) Field of Classification Search
CPC ............... A61B 46/20; A61F 13/00059; A61F 13/00063; A61F 13/00068; A61F 13/0206; (Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Office Action for related U.S. Appl. No. 15/997,809, dated Aug. 5, 2020.
(Continued)

*Primary Examiner* — Philip C Tucker
*Assistant Examiner* — Brian R Slawski

(57) ABSTRACT

Dressings for tissue treatment with negative pressure and methods of assembling the dressings for tissue treatment with negative pressure are disclosed. A method of assembling a dressing, which may comprise at least three layers assembled in a stacked relationship, may comprise providing an assembly station having at least one retaining pin, placing a first layer on the assembly station, placing a second layer on the assembly station, and bonding the second layer to the first layer. The first layer may comprise a plurality of apertures, at least some of which may be engaged by the retaining pins, and the second layer may comprise fluid restrictions and alignment areas for engaging with the retaining pins so that the fluid restrictions may be aligned with the apertures of the third layer.

14 Claims, 9 Drawing Sheets

Related U.S. Application Data filed on Feb. 21, 2018, provisional application No. 62/625,704, filed on Feb. 2, 2018, provisional application No. 62/623,325, filed on Jan. 29, 2018, provisional application No. 62/616,244, filed on Jan. 11, 2018, provisional application No. 62/615,821, filed on Jan. 10, 2018, provisional application No. 62/613,494, filed on Jan. 4, 2018, provisional application No. 62/592,950, filed on Nov. 30, 2017, provisional application No. 62/576,498, filed on Oct. 24, 2017, provisional application No. 62/565,754, filed on Sep. 29, 2017, provisional application No. 62/516,540, filed on Jun. 7, 2017, provisional application No. 62/516,550, filed on Jun. 7, 2017, provisional application No. 62/516,566, filed on Jun. 7, 2017.

(51) Int. Cl.

| | | |
|---|---|---|
| A61M 1/00 | (2006.01) | |
| A61L 15/26 | (2006.01) | |
| A61L 15/24 | (2006.01) | |
| B29C 65/78 | (2006.01) | |
| B32B 3/26 | (2006.01) | |
| B32B 27/06 | (2006.01) | |
| B32B 5/18 | (2006.01) | |
| B32B 27/32 | (2006.01) | |
| A61B 46/20 | (2016.01) | |
| A61L 15/52 | (2006.01) | |
| B29C 65/04 | (2006.01) | |
| B29L 31/00 | (2006.01) | |
| A61F 13/15 | (2006.01) | |
| A61F 13/511 | (2006.01) | |
| A61F 13/512 | (2006.01) | |
| A61F 13/513 | (2006.01) | |

(52) U.S. Cl.
CPC ...... *A61F 13/0206* (2013.01); *A61F 13/0213* (2013.01); *A61F 13/0216* (2013.01); *A61F 13/0223* (2013.01); *A61F 13/0263* (2013.01); *A61F 13/0289* (2013.01); *A61L 15/24* (2013.01); *A61L 15/26* (2013.01); *A61L 15/52* (2013.01); *A61M 1/0086* (2014.02); *A61M 1/0088* (2013.01); *B29C 65/7808* (2013.01); *B32B 3/266* (2013.01); *B32B 5/18* (2013.01); *B32B 27/065* (2013.01); *B32B 27/32* (2013.01); *A61F 13/00063* (2013.01); *A61F 2013/00319* (2013.01); *A61F 2013/00659* (2013.01); *A61F 2013/15406* (2013.01); *A61F 2013/5127* (2013.01); *A61F 2013/51139* (2013.01); *A61F 2013/51147* (2013.01); *A61F 2013/51322* (2013.01); *A61F 2013/51372* (2013.01); *A61L 2420/00* (2013.01); *A61M 2205/3344* (2013.01); *A61M 2205/584* (2013.01); *A61M 2207/00* (2013.01); *B29C 65/04* (2013.01); *B29L 2031/753* (2013.01); *B32B 2307/73* (2013.01); *B32B 2535/00* (2013.01)

(58) Field of Classification Search
CPC .............. A61F 13/0213; A61F 13/0216; A61F 13/0223; A61F 13/0263; A61F 13/0289; A61F 2013/00319; A61F 2013/00659; A61F 2013/15406; A61F 2013/51139; A61F 2013/51147; A61F 2013/5127; A61F 2013/51322; A61F 2013/51372; A61F 13/00029; A61F 13/022; A61L 15/24; A61L 15/26; A61L 15/52; A61L 2420/00; A61M 1/0086; A61M 1/0088; A61M 2205/3344; A61M 2205/584; A61M 2207/00; A61M 27/00; A61M 2210/1021; B29C 65/04; B29C 65/7808; B29C 65/00; B29C 65/48; B29C 65/78; B29C 65/7802; B29C 65/7805; B29C 65/7811; B29C 66/00; B29C 66/41; B29C 66/712; B29C 66/727; B29C 66/73181; B29C 66/73183; B29C 66/7392; B29L 2031/753; B32B 2307/73; B32B 2535/00; B32B 27/065; B32B 27/32; B32B 3/266; B32B 5/18

USPC ....... 156/60, 90, 91, 92, 250, 252, 256, 285, 156/286, 293, 349, 423; 604/289, 304, 604/313, 319, 543; 428/98, 131, 136, 428/137, 221, 343, 354

See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,173,046 | A | 11/1979 | Gallagher |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |

(56) References Cited

U.S. PATENT DOCUMENTS

| | | |
|---|---|---|
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A | 6/1997 | Fabo |
| 5,636,643 A | 6/1997 | Argenta et al. |
| 5,645,081 A | 7/1997 | Argenta et al. |
| 5,876,549 A * | 3/1999 | Natarajan ........... B32B 38/1841 156/249 |
| 5,981,822 A | 11/1999 | Addison |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1 | 2/2004 | Hunt et al. |
| 2004/0138604 A1 | 7/2004 | Sigurjonsson et al. |
| 2004/0148756 A1* | 8/2004 | Pommer ............... H05K 3/4638 29/466 |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2009/0047495 A1 | 2/2009 | Hubbs |
| 2009/0234307 A1 | 9/2009 | Vitaris |
| 2009/0293887 A1 | 12/2009 | Wilkes et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1 | 3/2010 | Olson |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0160686 A1 | 6/2011 | Ueda et al. |
| 2011/0213287 A1 | 9/2011 | Lattimore et al. |
| 2011/0224631 A1 | 9/2011 | Simmons et al. |
| 2011/0282309 A1 | 11/2011 | Adie et al. |
| 2011/0313374 A1 | 12/2011 | Lockwood et al. |
| 2012/0046603 A1 | 2/2012 | Vinton |
| 2012/0157945 A1 | 6/2012 | Robinson et al. |
| 2012/0209226 A1 | 8/2012 | Simmons et al. |
| 2012/0238932 A1 | 9/2012 | Atteia et al. |
| 2013/0030546 A1* | 1/2013 | Bandoh ................ A61L 27/443 623/23.34 |
| 2013/0053748 A1 | 2/2013 | Cotton |
| 2013/0087266 A1* | 4/2013 | Becerril ............... B32B 38/1841 156/92 |
| 2013/0261534 A1 | 10/2013 | Niezgoda et al. |
| 2014/0031771 A1 | 1/2014 | Locke et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0141941 A1 | 5/2015 | Allen et al. |
| 2015/0174291 A1 | 6/2015 | Zimnitsky et al. |
| 2015/0174304 A1 | 6/2015 | Askem et al. |
| 2015/0320602 A1 | 11/2015 | Locke et al. |

(56) References Cited

U.S. PATENT DOCUMENTS

| | | | |
|---|---|---|---|
| 2016/0000610 | A1 | 1/2016 | Riesinger |
| 2016/0015571 | A1 | 1/2016 | Robinson et al. |
| 2016/0022885 | A1 | 1/2016 | Dunn et al. |
| 2016/0144084 | A1 | 5/2016 | Collinson et al. |
| 2016/0144085 | A1 | 5/2016 | Melin et al. |
| 2016/0166744 | A1 | 6/2016 | Hartwell |
| 2016/0199550 | A1 | 7/2016 | Seddon et al. |
| 2016/0220742 | A1 | 8/2016 | Robinson et al. |
| 2016/0262672 | A1 | 9/2016 | Hammond et al. |
| 2016/0263776 | A1* | 9/2016 | Humfeld ............... B29B 15/12 |
| 2016/0354253 | A1 | 12/2016 | Hunt et al. |
| 2017/0079846 | A1 | 3/2017 | Locke et al. |
| 2017/0095374 | A1 | 4/2017 | Lauer |
| 2017/0172807 | A1 | 6/2017 | Robinson et al. |
| 2017/0312406 | A1 | 11/2017 | Svensby |
| 2017/0348154 | A1 | 12/2017 | Robinson et al. |
| 2018/0071148 | A1 | 3/2018 | Lockwood et al. |
| 2018/0289872 | A1 | 10/2018 | Coulthard et al. |
| 2019/0184075 | A1 | 6/2019 | Roos |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A | 9/1984 |
| EP | 0161865 A2 | 11/1985 |
| EP | 0174803 A2 | 3/1986 |
| EP | 0385302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2468905 A | 9/2010 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9319709 A1 | 10/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2007113597 A2 | 10/2007 |
| WO | 2010061228 A1 | 6/2010 |
| WO | 2011008497 A2 | 1/2011 |
| WO | 2011135286 A1 | 11/2011 |
| WO | 2014140608 A1 | 9/2014 |
| WO | 2015168681 A1 | 11/2015 |
| WO | 2015173547 A1 | 11/2015 |
| WO | 2015193257 A1 | 12/2015 |
| WO | 2016014645 A1 | 1/2016 |
| WO | 2016015001 A2 | 1/2016 |
| WO | 2017040045 A1 | 3/2017 |
| WO | 2017119996 A1 | 7/2017 |

OTHER PUBLICATIONS

Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Office Action for related U.S. Appl. No. 16/000,284, dated Jun. 8, 2020.
Office Action for related U.S. Appl. No. 15/997,833, dated Jun. 19, 2020.
3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.
3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N:5002385+4294834151&rt=d; accessed May 21, 2019>.
International Search Report and Written Opinion for related application PCT/US2018/036013, dated Aug. 7, 2018.
International Search Report and Written Opinion for related application PCT/US2018/035945, dated Aug. 24, 2018.
International Search Report and Written Opinion for related application PCT/US2018/036074, dated Aug. 24, 2018.
International Search Report and Written Opinion for related application PCT/US2018/035957, dated Sep. 28, 2018.
International Search Report and Written Opinion for related application PCT/US2018/035995, dated Oct. 1, 2018.
International Search Report and Written Opinion for related application PCT/US2018/036021, dated Aug. 24, 2018.
International Search Report and Written Opinion for related application PCT/US2018/036019, dated Oct. 18, 2018.
International Search Report and Written Opinion for related application PCT/US2018/036054, dated Aug. 24, 2018.
International Search Report and Written Opinion for related application PCT/US2018/036049, dated Aug. 29, 2018.
International Search Report and Written Opinion for related application PCT/US2018/036077, dated Aug. 24, 2018.
International Search Report and Written Opinion for related application PCT/US2018/036129, dated Oct. 8, 2018.
Heit, et al., "Foam Pore Size Is a Critical Interface Parameter of Suction-Based Wound Healing Devices," copyright 2012 by the American Society of Plastic Surgeons (www. PRSJournal.com) (Year: 2011).
Office Action for related U.S. Appl. No. 16/000,284, dated Sep. 23, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related application 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001 pp. 6646-6652.
Office Action for related U.S. Appl. No. 16/000,368, dated Dec. 14, 2020.

\* cited by examiner

ASSEMBLY FEATURES AND METHODS FOR A PEEL-AND-PLACE DRESSING FOR USE WITH NEGATIVE-PRESSURE TREATMENT

RELATED APPLICATION

This application claims the benefit, under 35 U.S.C. § 119(e), of the filing of U.S. Provisional Patent Application Ser. No. 62/650,572, entitled "ASSEMBLY FEATURES AND METHODS FOR A PEEL-AND-PLACE DRESSING FOR USE WITH NEGATIVE-PRESSURE TREATMENT," filed Mar. 30, 2018; U.S. Provisional Patent Application Ser. No. 62/633,438, entitled "COMPOSITE DRESSINGS FOR IMPROVED GRANULATION AND REDUCED MACERATION WITH NEGATIVE-PRESSURE TREATMENT," filed Feb. 21, 2018; U.S. Provisional Patent Application Ser. No. 62/623,325, entitled "METHODS FOR MANUFACTURING AND ASSEMBLING DUAL MATERIAL TISSUE INTERFACE FOR NEGATIVE-PRESSURE THERAPY," filed Jan. 29, 2018; U.S. Provisional Patent Application Ser. No. 62/625,704, entitled "CUSTOMIZABLE COMPOSITE DRESSINGS FOR IMPROVED GRANULATION AND REDUCED MACERATION WITH NEGATIVE-PRESSURE TREATMENT," filed Feb. 2, 2018; U.S. Provisional Patent Application Ser. No. 62/616,244, entitled "COMPOSITE DRESSINGS FOR IMPROVED GRANULATION AND REDUCED MACERATION WITH NEGATIVE-PRESSURE TREATMENT," filed Jan. 11, 2018; U.S. Provisional Patent Application Ser. No. 62/615,821, entitled "METHODS FOR MANUFACTURING AND ASSEMBLING DUAL MATERIAL TISSUE INTERFACE FOR NEGATIVE-PRESSURE THERAPY," filed Jan. 10, 2018; U.S. Provisional Patent Application Ser. No. 62/613,494, entitled "PEEL AND PLACE DRESSING FOR THICK EXUDATE AND INSTILLATION," filed Jan. 4, 2018; U.S. Provisional Patent Application Ser. No. 62/592,950, entitled "MULTI-LAYER WOUND FILLER FOR EXTENDED WEAR TIME," filed Nov. 30, 2017; U.S. Provisional Patent Application Ser. No. 62/576,498, entitled "SYSTEMS, APPARATUSES, AND METHODS FOR NEGATIVE-PRESSURE TREATMENT WITH REDUCED TISSUE IN-GROWTH," filed Oct. 24, 2017; U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to dressings for tissue treatment with negative pressure and methods of assembling and using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a method of assembling a composite dressing may include providing an assembly station having a plurality of retaining pins and placing a first layer having a plurality of apertures on the assembly station. The method may include engaging the retaining pins with at least some of the apertures to retain the first layer in at least one plane. The method may further include placing a second layer having a plurality of fluid restrictions and at least one alignment area on the assembly station. The alignment areas may be engaged with the retaining pins so that at least some of the fluid restrictions are centrally aligned with at least some of the apertures. Additionally, the method may include bonding the second layer to the first layer.

In some additional embodiments, a method of assembling a composite dressing may include providing an assembly station having a plurality of protruding forms and placing a gel layer having a plurality of apertures on the assembly station. The protruding forms may be inserted through at least some of the apertures to retain the gel layer in at least one plane. The method may further include placing a polymer film having at least two wings and a plurality of fluid restrictions over the gel layer on the assembly station, and the polymer film may be positioned so that the wings are in contact with all of the protruding forms. Additionally, the method may include bonding the polymer film to the gel layer.

In further embodiments, a method of assembling a composite dressing may include providing an assembly station having a plurality of protruding forms and placing a gel layer having a plurality of apertures on the assembly station. The protruding forms may be inserted through at least some of the apertures to retain the gel layer in at least one plane. The method may further include placing a polymer film having a plurality of fluid restrictions and at least two alignment apertures over the gel layer on the assembly station, and the protruding forms may be inserted through the alignment apertures. The method may further include bonding the polymer film to the gel layer.

In still further embodiments, a method of assembling a composite dressing may include placing a first layer on a means for retaining the first layer in at least one plane, placing a second layer adjacent to the first layer, and bonding the second layer to the first layer. The first layer may have a plurality of apertures, and the second layer may have a plurality of fluid restrictions and a means for aligning the fluid restrictions with the plurality of apertures.

In yet further embodiments, a dressing for treating a tissue site may include a first layer having a plurality of apertures, a second layer having a plurality of fluid restrictions, and a third layer comprising a foam. The second layer may be adapted to be positioned between the first layer and the third layer. The first layer may further include at least one alignment region having at least one alignment hole, and the second layer may include at least one alignment area. At least a portion of the at least one alignment area of the second layer may be configured to be positioned adjacent to at least a portion of the at least one alignment region of the first layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
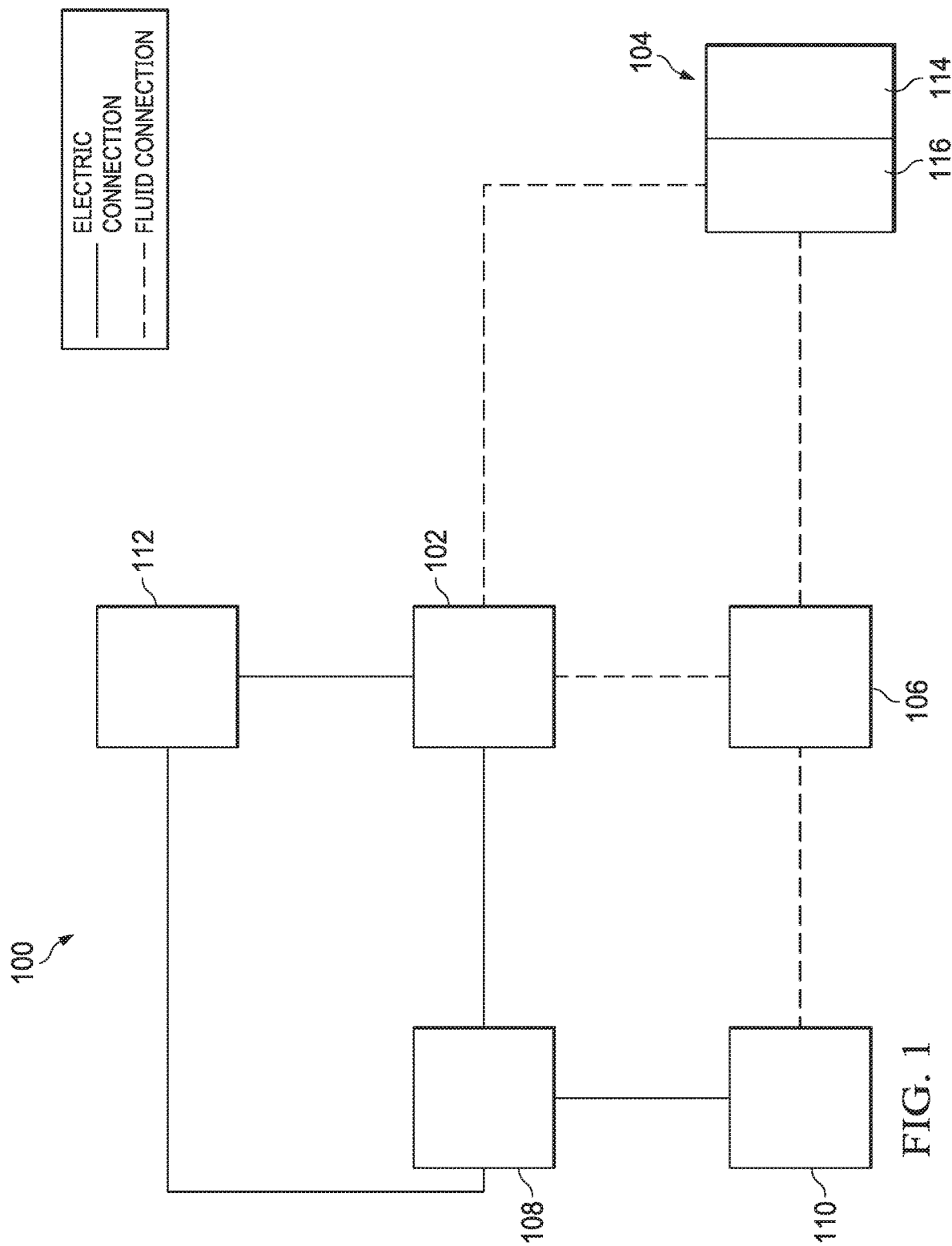
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. As illustrated in the example of FIG. 1, the dressing 104 may comprise or consist essentially of a tissue interface 114, a cover 116, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Tex.

The therapy system 100 may also include a regulator or controller, such as a controller 108. Additionally, the therapy system 100 may include sensors to measure operating parameters and provide feedback signals to the controller 108 indicative of the operating parameters. As illustrated in FIG. 1, for example, the therapy system 100 may include a first sensor 110 and a second sensor 112 coupled to the controller 108.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the controller 108 and other components into a therapy unit.

In general, components of the therapy system 100 may be coupled directly or indirectly. For example, the negative-pressure source 102 may be directly coupled to the container 106 and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 102, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 102 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the first sensor 110 and the second sensor 112, are generally known in the art as any apparatus operable to detect or measure a physical phenomenon or property, and generally provide a signal indicative of the phenomenon or property that is detected or measured. For example, the first sensor 110 and the second sensor 112 may be configured to measure one or more operating parameters of the therapy system 100. In some embodiments, the first sensor 110 may be a transducer configured to measure pressure in a pneumatic pathway and convert the measurement to a signal indicative of the pressure measured. In some embodiments, for example, the first sensor 110 may be a piezo-resistive strain gauge. The second sensor 112 may optionally measure operating parameters of the negative-pressure source 102, such as a voltage or current, in some embodiments. Preferably, the signals from the first sensor 110 and the second sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and have more than one layer in some embodiments. The tissue interface 114 may also have many sizes, shapes, or thicknesses, depending on a variety of factors, such as the type of treatment being implemented or the nature and size of a tissue site. For example, the size and shape of the tissue interface 114 may be adapted to the contours of deep and irregular shaped tissue sites. Any or all of the surfaces of the tissue interface 114 may have an uneven, coarse, or jagged profile.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may comprise or consist of, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 116 may comprise INSPIRE 2301 having an MVTR (upright cup technique) of 2600 g/m$^2$/24 hours and a thickness of about 30 microns.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 114 may be placed within, over, on, or otherwise proximate to a tissue site. If the tissue site is a wound, for example, the tissue interface 114 may partially or completely fill the wound, or it may be placed over the wound. The cover 116 may be placed over the tissue interface 114 and sealed to an attachment surface near a tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 114 in the sealed therapeutic environment can induce macro-strain and micro-strain in the tissue site. Negative pressure can also remove exudate and other fluid from a tissue site, which can be collected in container 106.

In some embodiments, the controller 108 may receive and process data from one or more sensors, such as the first sensor 110. The controller 108 may also control the operation of one or more components of the therapy system 100 to manage the pressure delivered to the tissue interface 114. In some embodiments, controller 108 may include an input for receiving a desired target pressure and may be programmed for processing data relating to the setting and inputting of the target pressure to be applied to the tissue interface 114. In some example embodiments, the target pressure may be a fixed pressure value set by an operator as the target negative pressure desired for therapy at a tissue site and then provided as input to the controller 108. The target pressure may vary from tissue site to tissue site based on the type of tissue forming a tissue site, the type of injury or wound (if any), the medical condition of the patient, and the preference of the attending physician. After selecting a desired target pressure, the controller 108 can operate the negative-pressure source 102 in one or more control modes based on the target pressure and may receive feedback from one or more sensors to maintain the target pressure at the tissue interface 114.

Figure 2:
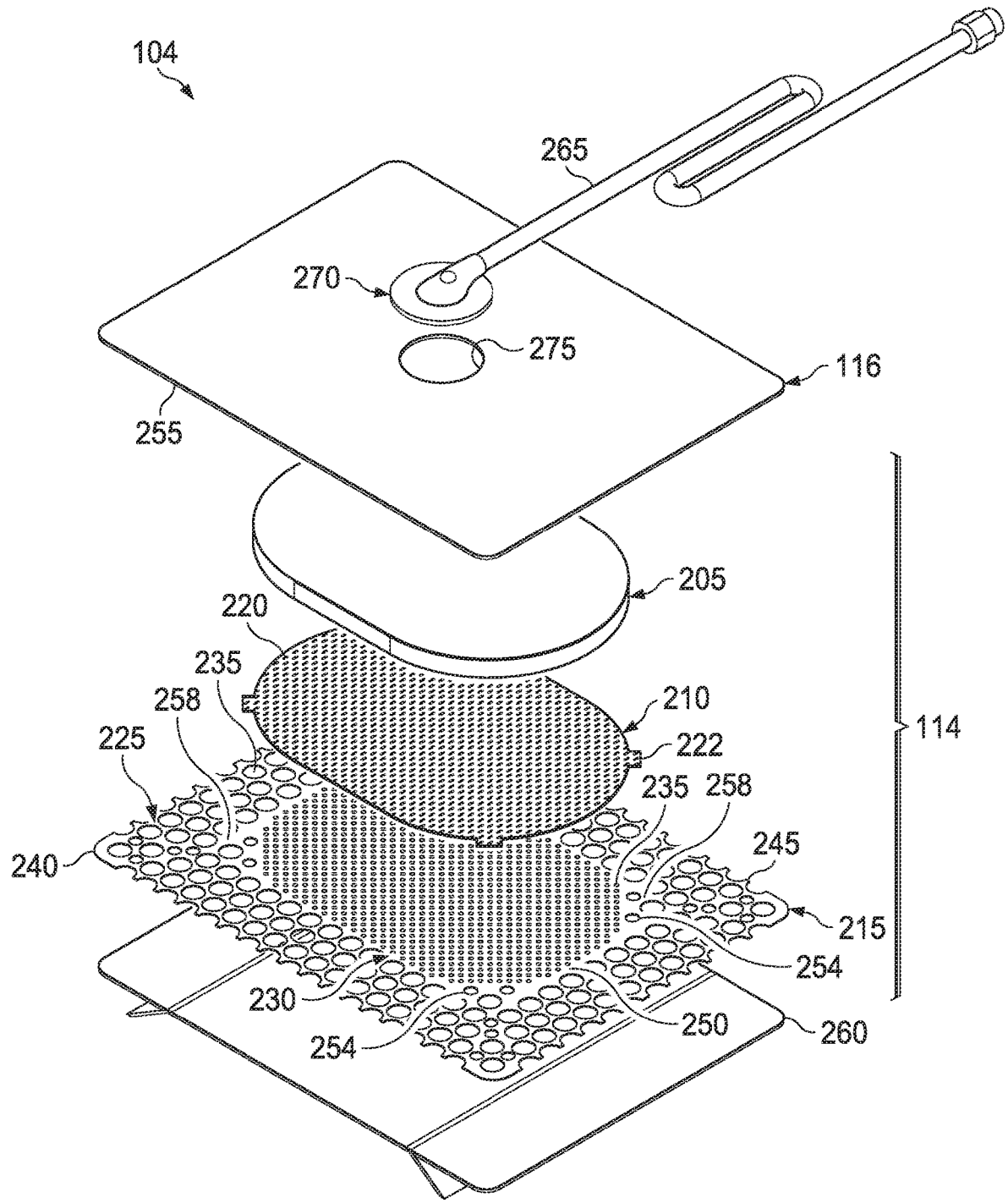
FIG. 2 is an assembly view of an example of a dressing, illustrating additional details that may be associated with some example embodiments of the therapy system of FIG. 1.

FIG. 2 is an assembly view of an example of the dressing 104 of FIG. 1, illustrating additional details that may be associated with some embodiments in which the tissue interface 114 comprises more than one layer. In the example of FIG. 2, the tissue interface 114 comprises a first layer 205, a second layer 210, and a third layer 215. In some embodiments, the first layer 205 may be disposed adjacent to a second layer 210, and the third layer 215 may be disposed adjacent to the second layer 210 opposite the first layer 205. For example, the first layer 205, the second layer 210, and the third layer 215 may be stacked so that the first layer 205 is in contact with the second layer 210, and the second layer 210 is in contact with the first layer 205 and the third layer 215. One or more of the first layer 205, the second layer 210, and the third layer 215 may also be bonded to an adjacent layer in some embodiments.

The first layer 205 may comprise or consist essentially of a manifold or manifold layer, which provides a means for collecting or distributing fluid across the tissue interface 114 under pressure. For example, the first layer 205 may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 114.

In some illustrative embodiments, the first layer 205 may comprise a plurality of pathways, which can be interconnected to improve distribution or collection of fluids. In some embodiments, the first layer 205 may comprise or consist essentially of a porous material having interconnected fluid pathways. For example, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the first layer 205 may additionally or alternatively comprise projections that form interconnected fluid pathways. For example, the first layer 205 may be molded to provide surface projections that define interconnected fluid pathways. Any or all of the surfaces of the first layer 205 may have an uneven, coarse, or jagged profile In some embodiments, the first layer 205 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the first layer 205 may also vary according to needs of a prescribed therapy. For example, the tensile strength of a foam may be increased for instillation of topical treatment solutions. The 25% compression load deflection of the first layer 205 may be at least 0.35 pounds per square inch, and the 65% compression load deflection may be at least 0.43 pounds per square inch. In some embodiments, the tensile strength of the first layer 205 may be at least 10 pounds per square inch. The first layer 205 may have a tear strength of at least 2.5 pounds per inch. In some embodiments, the first layer 205 may be a foam comprised of polyols such as polyester or polyether, isocyanate such as toluene diisocyanate, and polymerization modifiers such as amines and tin compounds. In one non-limiting example, the first layer 205 may be a reticulated polyurethane ether foam such as used in GRANUFOAM™ dressing or V.A.C. VERAFLO™ dressing, both available from KCI of San Antonio, Tex.

The first layer 205 generally has a first planar surface and a second planar surface opposite the first planar surface. The thickness of the first layer 205 between the first planar surface and the second planar surface may also vary according to needs of a prescribed therapy. For example, the thickness of the first layer 205 may be decreased to relieve stress on other layers and to reduce tension on peripheral tissue. The thickness of the first layer 205 can also affect the conformability of the first layer 205. In some embodiments, a thickness in a range of about 5 millimeters to 10 millimeters may be suitable.

The second layer 210 may comprise or consist essentially of a means for controlling or managing fluid flow. In some embodiments, the second layer may comprise or consist essentially of a liquid-impermeable, elastomeric material. For example, the second layer 210 may comprise or consist essentially of a polymer film. The second layer 210 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer may have a substantially flat surface, with height variations limited to 0.2 millimeters over a centimeter.

In some embodiments, the second layer 210 may be hydrophobic. The hydrophobicity of the second layer 210 may vary, but may have a contact angle with water of at least ninety degrees in some embodiments. In some embodiments the second layer 210 may have a contact angle with water of no more than 150 degrees. For example, in some embodiments, the contact angle of the second layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the second layer 210 may be further enhanced with a hydrophobic coating of other materials, such as silicones and fluorocarbons, either as coated from a liquid, or plasma coated.

The second layer 210 may also be suitable for welding to other layers, including the first layer 205. For example, the second layer 210 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the second layer 210 may vary according to a prescribed therapy or application. In some embodiments, an area density of less than 40 grams per square meter may be suitable, and an area density of about 20-30 grams per square meter may be particularly advantageous for some applications.

In some embodiments, for example, the second layer 210 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the second layer 210 may have one or more fluid restrictions 220, which can be distributed uniformly or randomly across the second layer 210. The fluid restrictions 220 may be bi-directional and pressure-responsive. For example, the fluid restrictions 220 can generally comprise or consist essentially of an elastic passage that is normally unstrained to substantially reduce liquid flow, and can expand in response to a pressure gradient. In some embodiments, the fluid restrictions 220 may comprise or consist essentially of perforations in the second layer 210. Perforations may be formed by removing material from the second layer 210. For example, perforations may be formed by cutting through the second layer 210, which may also deform the edges of the perforations in some embodiments. In the absence of a pressure gradient across the perforations, the passages may be sufficiently small to form a seal or flow restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the second layer 210 may be a suitable valve for some applications. Fenestrations may also be formed by removing material from the second layer 210, but the amount of material removed and the resulting dimensions of the fenestrations may be an order of magnitude less than perforations, and may not deform the edges.

For example, some embodiments of the fluid restrictions 220 may comprise or consist essentially of one or more slots or combinations of slots in the second layer 210. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

As shown in the example of FIG. 2, the second layer 210 may also include one or more alignment areas 222, which may be designed to assist with aligning the second layer 210 with a portion of the third layer 215. As shown in FIG. 2, the alignment areas 222 may be in the form of appendages, such as wings or tabs that may protrude from or extend from the perimeter of the second layer 210. Some embodiments of the second layer 210 may include alignment areas 222 that do not protrude from the perimeter of the second layer 210, but rather are segments or specific area(s) of the second layer 210.

The third layer 215 may be a sealing layer comprising or consisting essentially of a soft, pliable material suitable for providing a fluid seal with a tissue site, and may have a substantially flat surface. For example, the third layer 215 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the third layer 215 may have a thickness between about 200 microns ($\mu$m) and about 1000 microns ($\mu$m). In some embodiments, the third layer 215 may have a hardness between about 5 Shore 00 and about 80 Shore OO. Further, the third layer 215 may be comprised of hydrophobic or hydrophilic materials.

In some embodiments, the third layer 215 may be a hydrophobic-coated material. For example, the third layer 215 may be formed by coating a spaced material, such as, for example, woven, nonwoven, molded, or extruded mesh with a hydrophobic material. The hydrophobic material for the coating may be a soft silicone, for example.

The third layer 215 may have a peripheral area, such as a periphery 225, surrounding or around a central area, such as an interior portion 230, and apertures 235 disposed through the periphery 225 and the interior portion 230. The interior portion 230 may correspond to a surface area of the first layer 205 in some examples. The third layer 215 may also have corners 240 and edges 245. The corners 240 and the edges 245 may be part of the periphery 225. The third layer 215 may have an interior border 250 around the interior portion 230, disposed between the interior portion 230 and the periphery 225. The interior border 250 may be substantially free of the apertures 235, as illustrated in the example of FIG. 2. In some examples, as illustrated in FIG. 2, the interior portion 230 may be symmetrical and centrally disposed in the third layer 215.

The apertures 235 may be formed by cutting or by application of local RF or ultrasonic energy, for example, or by other suitable techniques for forming an opening. The apertures 235 may have a uniform distribution pattern, or may be randomly distributed on the third layer 215. The apertures 235 in the third layer 215 may have many shapes, including circles, squares, stars, ovals, polygons, slits, complex curves, rectilinear shapes, triangles, for example, or may have some combination of such shapes.

Each of the apertures 235 may have uniform or similar geometric properties. For example, in some embodiments, each of the apertures 235 may be circular apertures, having substantially the same diameter. In some embodiments, the diameter of each of the apertures 235 may be between about 1 millimeter to about 50 millimeters. In other embodiments, the diameter of each of the apertures 235 may be between about 1 millimeter to about 20 millimeters.

In other embodiments, geometric properties of the apertures 235 may vary. For example, the diameter of the apertures 235 may vary depending on the position of the apertures 235 in the third layer 215, as illustrated in FIG. 2. In some embodiments, the diameter of the apertures 235 in the periphery 225 of the third layer 215 may be larger than the diameter of the apertures 235 in the interior portion 230 of the third layer 215. For example, in some embodiments, the apertures 235 disposed in the periphery 225 may have a diameter between about 9.8 millimeters to about 10.2 millimeters. In some embodiments, the apertures 235 disposed in the corners 240 may have a diameter between about 7.75 millimeters to about 8.75 millimeters. In some embodiments, the apertures 235 disposed in the interior portion 230 may have a diameter between about 1.8 millimeters to about 2.2 millimeters.

At least one of the apertures 235 in the periphery 225 of the third layer 215 may be positioned at the edges 245 of the periphery 225, and may have an interior cut open or exposed at the edges 245 that is in fluid communication in a lateral direction with the edges 245. The lateral direction may refer to a direction toward the edges 245 and in the same plane as the third layer 215. As shown in the example of FIG. 2, the apertures 235 in the periphery 225 may be positioned proximate to or at the edges 245 and in fluid communication in a lateral direction with the edges 245. The apertures 235 positioned proximate to or at the edges 245 may be spaced substantially equidistant around the periphery 225 as shown in the example of FIG. 2. Alternatively, the spacing of the apertures 235 proximate to or at the edges 245 may be irregular.

Additionally, in some embodiments, the third layer 215 may further include one or more registration apertures, such as alignment holes 254, which may be useful for facilitating alignment of the second layer 210 and the third layer 215 during manufacturing and/or assembly of the tissue interface 114. For example, the alignment holes 254 may be positioned in corner regions of the interior border 250 of the third layer 215, such as alignment regions 258 that may otherwise be substantially free of apertures or holes. The exact number and positioning of the alignment holes 254 may vary; however, in some instances the alignment holes 254 may include two holes or apertures in each of the four corner regions of the interior border 250, as shown in FIG. 2, for a total of eight holes. As also depicted in the illustrative embodiment of FIG. 2, the alignment holes 254 may be positioned adjacent to a set of three apertures 235 of the periphery 225, which may span along the curvatures of the four corners of the interior border 250.

In the example of FIG. 2, the dressing 104 may further include an attachment device, such as an adhesive 255. The adhesive 255 may be, for example, a medically-acceptable, pressure-sensitive adhesive that extends about a periphery, a portion, or the entire cover 116. In some embodiments, for example, the adhesive 255 may be an acrylic adhesive having a coating weight between 25-65 grams per square meter (g.s.m.). Thicker adhesives, or combinations of adhesives, may be applied in some embodiments to improve the seal and reduce leaks. The adhesive 255 may be a layer having substantially the same shape as the periphery 225. In some embodiments, such a layer of the adhesive 255 may be continuous or discontinuous. Discontinuities in the adhesive 255 may be provided by apertures or holes (not shown) in the adhesive 255. The apertures or holes in the adhesive 255 may be formed after application of the adhesive 255 or by coating the adhesive 255 in patterns on a carrier layer, such as, for example, a side of the cover 116. Apertures or holes in the adhesive 255 may also be sized to enhance the MVTR of the dressing 104 in some example embodiments.

As illustrated in the example of FIG. 2, in some embodiments, a release liner 260 may be attached to or positioned adjacent to the third layer 215 to protect the adhesive 255 prior to use. The release liner 260 may also provide stiffness to assist with, for example, deployment of the dressing 104. The release liner 260 may be, for example, a casting paper, a film, or polyethylene. Further, in some embodiments, the release liner 260 may be a polyester material such as polyethylene terephthalate (PET), or similar polar semi-crystalline polymer. The use of a polar semi-crystalline polymer for the release liner 260 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. In some embodiments, the release liner 260 may have a surface texture that may be imprinted on an adjacent layer, such as the third layer 215. Further, a release agent may be disposed on a side of the release liner 260 that is configured to contact the third layer 215. For example, the release agent may be a silicone coating and may have a release factor suitable to facilitate removal of the release liner 260 by hand and without damaging or deforming the dressing 104. In some embodiments, the release agent may be a fluorocarbon or a fluorosilicone, for example. In other embodiments, the release liner 260 may be uncoated or otherwise used without a release agent.

FIG. 2 also illustrates one example of a fluid conductor 265 and a dressing interface 270. As shown in the example of FIG. 2, the fluid conductor 265 may be a flexible tube, which can be fluidly coupled on one end to the dressing interface 270. The dressing interface 270 may be an elbow connector, as shown in the example of FIG. 2, which can be placed over an aperture 275 in the cover 116 to provide a fluid path between the fluid conductor 265 and the tissue interface 114.

Figure 3:
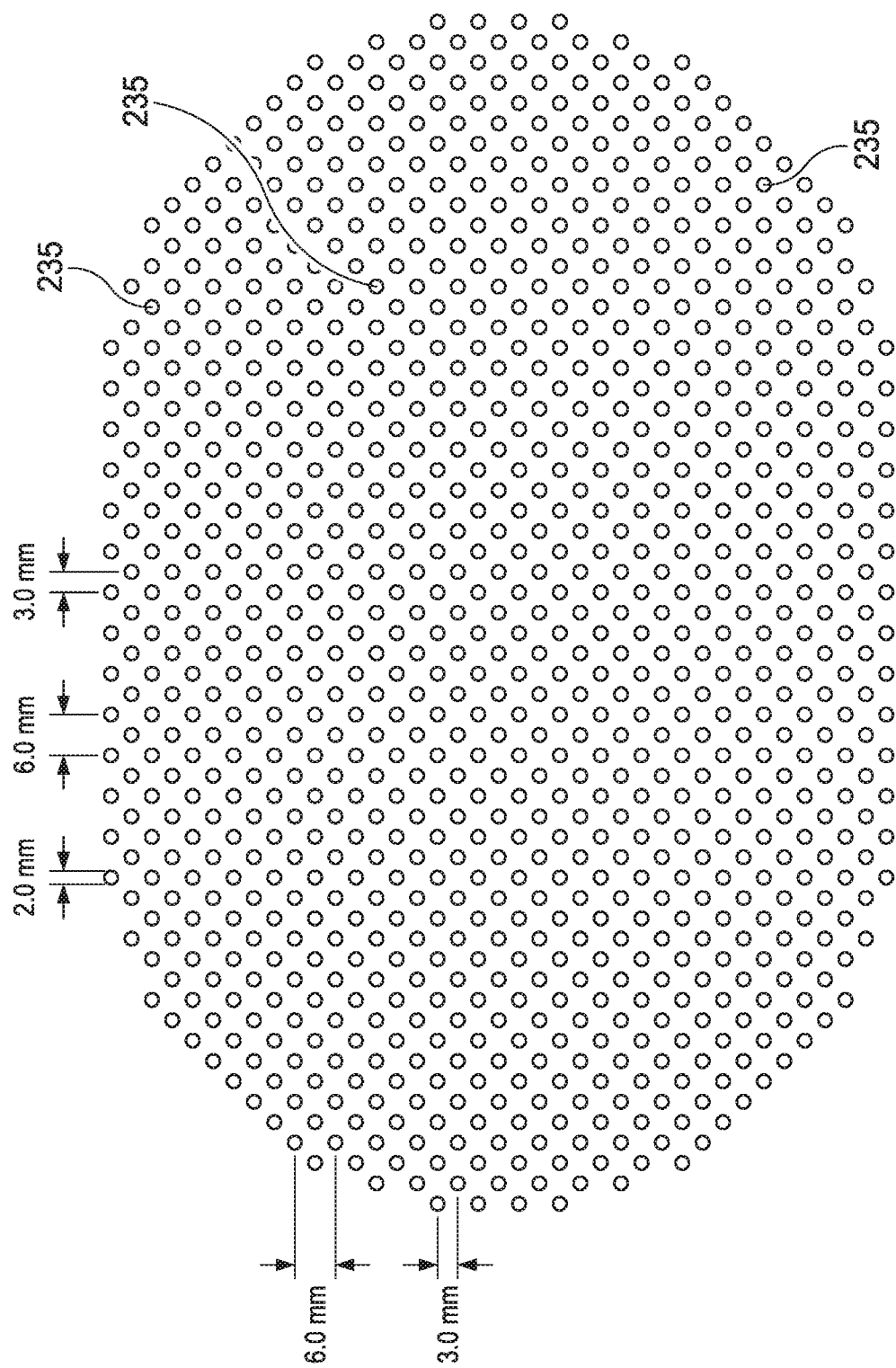
FIG. 3 is a schematic view of an example configuration of apertures in a layer of the dressing of FIG. 2, illustrating additional details that may be associated with some embodiments.

FIG. 3 is a schematic view of an example configuration of the apertures 235, illustrating additional details that may be associated with some embodiments of the third layer 215. In some embodiments, the apertures 235 illustrated in FIG. 3 may be associated only with the interior portion 230. In the example of FIG. 3, the apertures 235 are generally circular and have a diameter of about 2 millimeters. FIG. 3 also illustrates an example of a uniform distribution pattern of the apertures 235 in the interior portion 230. In FIG. 3, the apertures 235 are distributed across the interior portion 230 in a grid of parallel rows and columns. Within each row and column, the apertures 235 may be equidistant from each other, as illustrated in the example of FIG. 3. FIG. 3 illustrates one example configuration that may be particularly suitable for many applications, in which the apertures 235 are spaced about 6 millimeters apart along each row and column, with a 3 millimeter offset.

Figure 4:
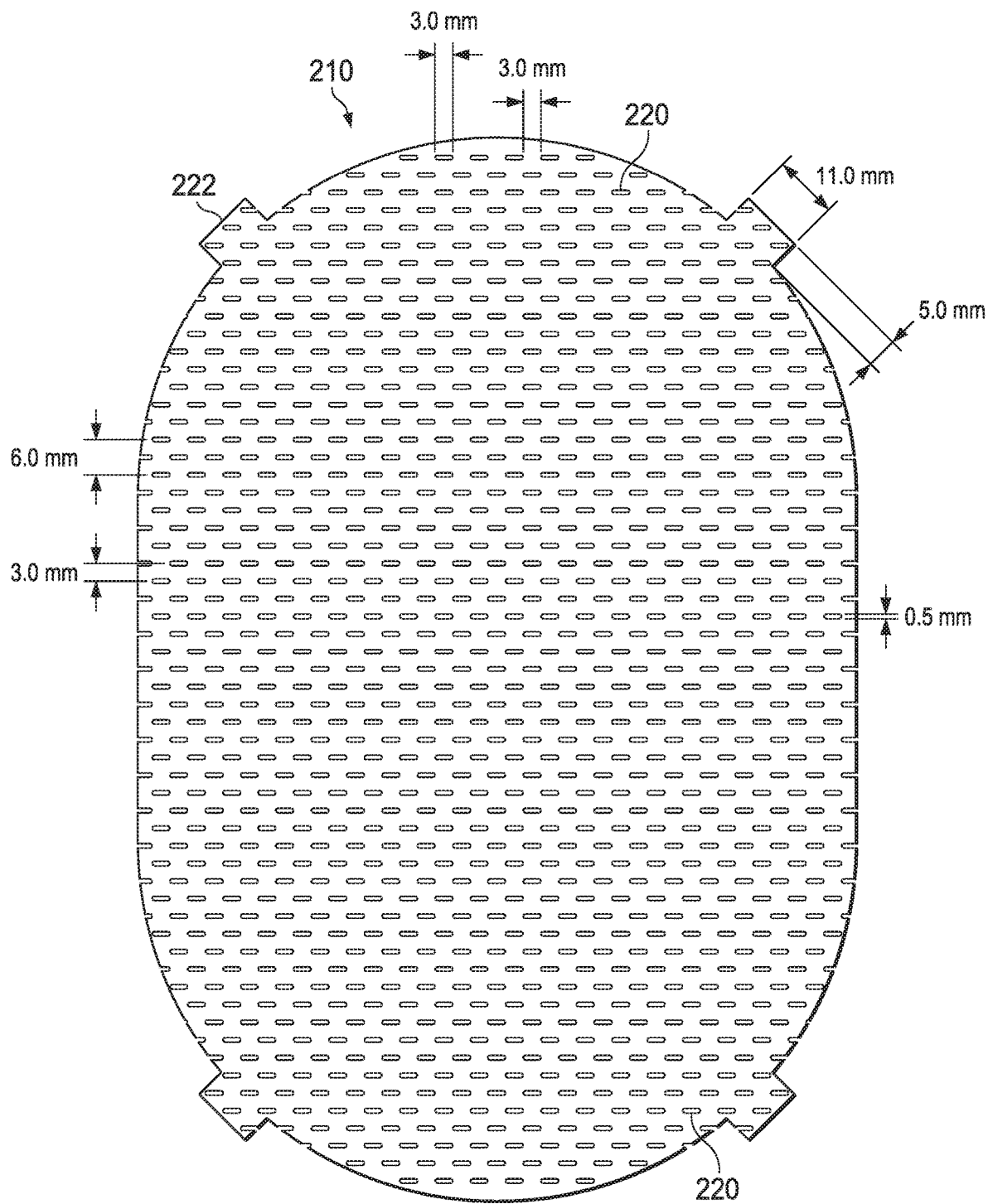
FIG. 4 is a schematic view of an example configuration of fluid restrictions in another layer that may be associated with some embodiments of the dressing of FIG. 2.

FIG. 4 is a schematic view of an example of the second layer 210, illustrating additional details that may be associated with some embodiments. As illustrated in the example of FIG. 4, the fluid restrictions 220 may each consist essentially of one or more linear slots having a length of about 3 millimeters. FIG. 4 additionally illustrates an example of a uniform distribution pattern of the fluid restrictions 220. In FIG. 4, the fluid restrictions 220 are substantially coextensive with the second layer 210, and are distributed across the second layer 210 in a grid of parallel rows and columns, in which the slots are also mutually parallel to each other. In some embodiments, the rows may be spaced about 3 millimeters on center, and the fluid restrictions 220 within each of the rows may be spaced about 3 millimeters on center as illustrated in the example of FIG. 4. The fluid restrictions 220 in adjacent rows may be aligned or offset. For example, adjacent rows may be offset, as illustrated in FIG. 4, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

The alignment areas 222 of FIG. 4 are shown as wings that protrude from or extend beyond the perimeter of the second layer 210. The alignment areas 222 may facilitate alignment with features of both the third layer 215 as well as tools used in the manufacture and/or assembly of the tissue interface 114. In some embodiments where the alignment areas 222 comprise wings, the wings may have a width of between 5 mm and 20 mm, and may protrude from the edge of the second layer 210 by a length of between 2 mm and 12 mm. For example, as shown in FIG. 4, the alignment areas 222 may comprise wings having a width of 11 mm and a length of 5 mm. As depicted in FIG. 4, the alignment areas 222 of the second layer 210 may include one or more of the fluid restrictions 220; however, the fluid restrictions 220 may not be disposed on all or any of the alignment areas 222. FIG. 4 illustrates an embodiment of a second layer 210 comprising four alignment areas 222 in the form of wings; however, other examples may include a greater or lesser number of alignment areas 222. The positioning of the alignment areas 222 may also be varied. Regardless of the number or size of alignment areas 222, the fluid restrictions 220 should be registered to or correspond to the position and area of the alignment areas 222 so that when the alignment areas 222 are used to correctly position the second layer 210, the fluid restrictions 220 will align with apertures 235 of the third layer 215. Alternatively or additionally, in some embodiments, the alignment areas 222 comprising wings may include an additional hole or perforation that may be larger than the fluid restrictions 220. For example, the additional hole may have a diameter of between about 1 mm and 2 mm, and may be large enough for the vision or scanning components of an automated assembly tool to detect. In some instances, the additional hole may be formed in the center of the wing of the alignment area 222.

Figure 5:
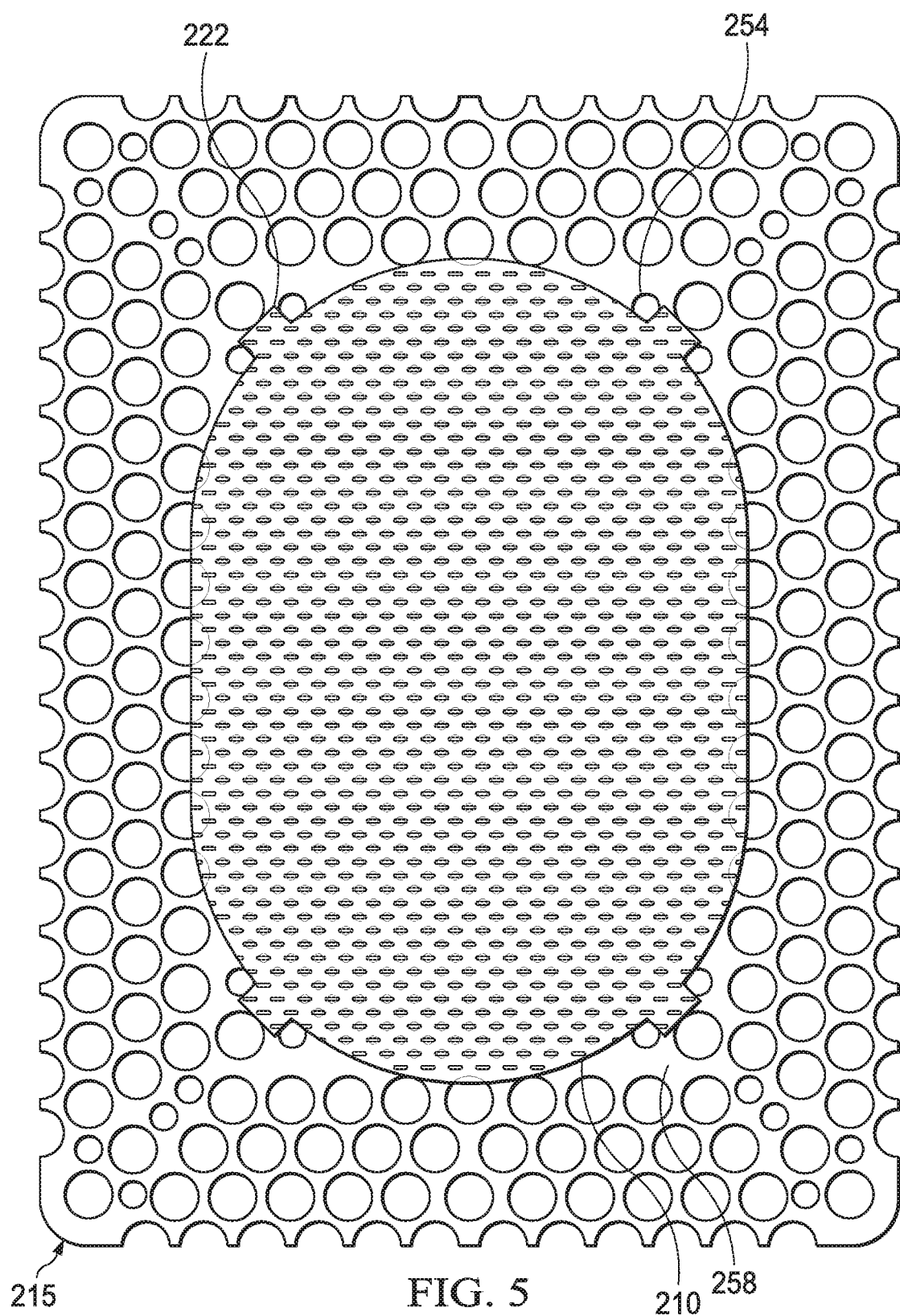
FIG. 5 is a schematic view of the example layer of FIG. 4 overlaid on the example layer of FIG. 3.

FIG. 5 is a schematic view of the second layer 210 of FIG. 4 overlaid on the third layer 215 of FIG. 2, illustrating additional details that may be associated with some example embodiments of the tissue interface 114. For example, as illustrated in FIG. 5, the fluid restrictions 220 may be aligned, overlapping, in registration with, or otherwise fluidly coupled to the apertures 235 in some embodiments. In some embodiments, one or more of the fluid restrictions 220 may be registered with the apertures 235 only in the interior portion 230 of the third layer 215. The fluid restrictions 220 in the example of FIG. 5 are generally configured so that each of the fluid restrictions 220 is registered with only one of the apertures 235. In other examples, one or more of the fluid restrictions 220 may be registered with more than one of the apertures 235. For example, any one or more of the fluid restrictions 220 may be a perforation or a fenestration that extends across two or more of the apertures 235. Additionally or alternatively, one or more of the fluid restrictions 220 may not be registered with any of the apertures 235.

As illustrated in the example of FIG. 5, the apertures 235 may be sized to expose a portion of the second layer 210, the fluid restrictions 220, or both through the third layer 215. In some embodiments, each of the apertures 235 may be sized to expose no more than two of the fluid restrictions 220. In some examples, the length of each of the fluid restrictions 220 may be substantially equal to or less than the diameter of each of the apertures 235. In some embodiments, the average dimensions of the fluid restrictions 220 are substantially similar to the average dimensions of the apertures 235. For example, the apertures 235 may be elliptical in some embodiments, and the length of each of the fluid restrictions 220 may be substantially equal to the major axis or the minor axis. In some embodiments, though, the dimensions of the fluid restrictions 220 may exceed the dimensions of the apertures 235, and the size of the apertures 235 may limit the effective size of the fluid restrictions 220 exposed to the lower surface of the dressing 104.

As also illustrated in the example of FIG. 5, when the second layer 210 is overlaid on the third layer 215, the alignment areas 222, such as the wings, may align with a solid area, or non-perforated or non-apertured region of the third layer 215 that is located between apertures on the third layer 215. For example, the alignment areas 222, such as wings, of the second layer 210 may be positioned between alignment holes 254 associated with alignment regions 258 of the third layer 215, which may be in one or more of the corner regions of the interior border 250 of the third layer 215. As shown in FIG. 5, each of the four alignment areas 222 of the second layer 210 may be positioned against an alignment region 258 of the third layer 215 and between two of the alignment holes 254. The alignment regions 258 may typically be portions of the third layer 215 that are not perforated and may be a solid material, such as a silicone material. The alignment regions 258 may include a region between two alignment holes 254, with each of the alignment holes 254 having a diameter of between 4 mm and 10 mm. In some embodiments, the alignment holes 254 may each have a diameter of approximately 6 mm.

Each of the second layer 210 and third layer 215 may be sized and scaled so that when each of the alignment areas 222 are properly positioned over the alignment regions 258 and between the alignment holes 254, the second layer 210 and third layer 215 may align so that fluid restrictions 220 of the second layer 210 are aligned with apertures 235 of the interior portion 230 of the third layer 215. The correct alignment of the layers may ensure proper registration of the fluid restrictions 220 with the apertures 235. The alignment areas 222 may facilitate alignment of the fluid restrictions 220 and the apertures 235 by engaging with a structure of an assembly tool used for assembly of the tissue interface 114. For example, the third layer 215 may be placed on an assembly tool such that rods or retaining pins of the assembly tool may extend through each of the eight alignment holes 254 of the third layer 215. When the second layer 210 is subsequently overlaid on the third layer 215 such that each of the alignment areas 222, such as the wings of FIG. 5, are positioned over an alignment region 258 of the third layer 215, each of the wings may touch the two rods or retaining pins extending through the adjacent alignment holes 254. The rods or pins may provide guides or boundaries between which the alignment areas 222 may be positioned. The alignment areas 222, such as the wings, may each fit between two of the assembly rods or pins, without being creased or buckled. The second layer 210 and the third layer 215 may be scaled to each other so that when the alignment areas 222 are properly positioned between the rods or pins, the fluid restrictions 220 may be aligned and registered with the apertures 235 of the third layer 215 in both X- and Y-axes. Once placed in contact with an alignment region 258 of the third layer 215, the alignment areas 222, as well as the other portions of the second layer 210, may be held in the proper overlaid position on the third layer 215, with the fluid restrictions 220 and apertures 235 in proper alignment, due to a silicone bond provided by the third layer 215.

In some alternative embodiments, the second layer 210 may be aligned with the third layer 215 by aligning an additional guide hole included as part of the second layer 210 with an alignment hole 254 of the third layer 215. For example, the second layer 210 and the third layer 215 may be configured such that when the two layers are overlaid in a proper position, the additional guide hole of the second layer 210 may be aligned or positioned adjacent to or over an alignment hole 254 of the third layer 215. In some embodiments, the guide hole of the second layer 210 may be sized so that when the second layer 210 is aligned over the third layer 215, the guide hole of the second layer 210 is coextensive with an alignment hole 254 of the third layer 215. The additional guide hole of the second layer 210 may be a different shape than the fluid restrictions 220 of the second layer 210 for easier identification. The shape itself of the guide hole of the second layer 210 may also facilitate alignment. The shape of the alignment hole 254 of the third layer 215 may also be different than that of the apertures 235 of the third layer 215 for easier identification. In some embodiments, the alignment hole 254 of the third layer 215 may be larger than the corresponding guide hole of the second layer 210, which may enable an automated assembly system to adjust the positioning of the second layer 210 and third layer 215 as the two layers are brought into alignment.

Regardless of the particular embodiments of the alignment features included as part of the second layer 210 and third layer 215 of the tissue interface 114, the first layer 205, which may comprise an open-cell foam, may be placed on top of the second layer 210 subsequent to alignment of the second layer 210 and third layer 215. In some embodiments, the first layer 205 may be sized and positioned adjacent a top surface of the second layer 210 to be substantially coextensive with the second layer 210, exclusive of alignment areas 222 comprising the wings, as well as the interior portion 230 of the third layer 215. The cover 116 may then be placed on top of the first layer 205, with the borders of the cover 116 placed around the first layer 205 and second layer 210 and compressed into silicone material of the third layer 215 to form a bond. The adhesive 255 of the cover 116 may pass through any exposed apertures 235 of the third layer 215, as well as any exposed fluid restrictions 220 of the second layer 210.

One or more of the components of the dressing 104 may additionally be treated with an antimicrobial agent in some embodiments. For example, the first layer 205 may be a foam, mesh, or non-woven coated with an antimicrobial agent. In some embodiments, the first layer may comprise antimicrobial elements, such as fibers coated with an antimicrobial agent. Additionally or alternatively, some embodiments of the second layer 210 may be a polymer coated or mixed with an antimicrobial agent. In other examples, the fluid conductor 265 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the first layer 205 may be a foam coated with such a mixture.

Individual components of the dressing 104 may be bonded or otherwise secured to one another with a solvent or non-solvent adhesive, or with thermal welding, for example, without adversely affecting fluid management. Further, the second layer 210 or the first layer 205 may be coupled to the interior border 250 of the third layer 215 in any suitable manner, such as with a weld or an adhesive, for example.

The cover 116, the first layer 205, the second layer 210, the third layer 215, or various combinations may be assembled before application or in situ. For example, the cover 116 may be laminated to the first layer 205, and the second layer 210 may be laminated to the first layer 205 opposite the cover 116 in some embodiments. The third layer 215 may also be coupled to the second layer 210 opposite the first layer 205 in some embodiments. In some embodiments, one or more layers of the tissue interface 114 may coextensive. In some embodiments, the second layer 210, the third layer 215, or both may overlap the edge of the first layer 205. In other embodiments, the second layer 210, the third layer 215, or both may be cut flush with the edge of the first layer 205, exposing the edge of the first layer 205.

For example, the first layer 205 may be coextensive with the second layer 210, as illustrated in the embodiment of FIG. 2. In some embodiments, the dressing 104 may be provided as a single, composite dressing. For example, the third layer 215 may be coupled to the cover 116 to enclose the first layer 205 and the second layer 210, wherein the third layer 215 is configured to face a tissue site. Additionally or alternatively, the second layer 210, the third layer 215, or some combination of the second layer 210 and the third layer 215 may be disposed on both sides of the first layer 205.

In use, the release liner 260 (if included) may be removed to expose the third layer 215, which may be placed within, over, on, or otherwise proximate to a tissue site, particularly a surface tissue site and adjacent epidermis. The third layer 215 and the second layer 210 may be interposed between the first layer 205 and the tissue site, which can substantially reduce or eliminate adverse interaction with the first layer 205. For example, the third layer 215 may be placed over a surface wound (including edges of the wound) and undamaged epidermis to prevent direct contact with the first layer 205. Treatment of a surface wound or placement of the dressing 104 on a surface wound includes placing the dressing 104 immediately adjacent to the surface of the body or extending over at least a portion of the surface of the body. Treatment of a surface wound does not include placing the dressing 104 wholly within the body or wholly under the surface of the body, such as placing a dressing within an abdominal cavity. In some applications, the interior portion 230 of the third layer 215 may be positioned adjacent to, proximate to, or covering a tissue site. In some applications, at least some portion of the second layer 210, the fluid restrictions 220, or both may be exposed to a tissue site through the third layer 215. The periphery 225 of the third layer 215 may be positioned adjacent to or proximate to tissue around or surrounding the tissue site. The third layer 215 may be sufficiently tacky to hold the dressing 104 in position, while also allowing the dressing 104 to be removed or re-positioned without trauma to the tissue site.

Removing the release liner 260 can also expose the adhesive 255, and the cover 116 may be attached to an attachment surface. For example, the cover 116 may be attached to epidermis peripheral to a tissue site, around the first layer 205 and the second layer 210. The adhesive 255 may be in fluid communication with an attachment surface through the apertures 235 in at least the periphery 225 of the third layer 215 in some embodiments. The adhesive 255 may also be in fluid communication with the edges 245 through the apertures 235 exposed at the edges 245.

Once the dressing 104 is in the desired position, the adhesive 255 may be pressed through the apertures 235 to bond the dressing 104 to the attachment surface. The apertures 235 at the edges 245 may permit the adhesive 255 to flow around the edges 245 for enhancing the adhesion of the edges 245 to an attachment surface.

In some embodiments, apertures or holes in the third layer 215 may be sized to control the amount of the adhesive 255 in fluid communication with the apertures 235. For a given geometry of the corners 240, the relative sizes of the apertures 235 may be configured to maximize the surface area of the adhesive 255 exposed and in fluid communication through the apertures 235 at the corners 240. For example, as shown in FIG. 2, the edges 245 may intersect at substantially a right angle, or about 90 degrees, to define the corners 240. In some embodiments, the corners 240 may have a radius of about 10 millimeters. Further, in some embodiments, three of the apertures 235 having a diameter between about 7.75 millimeters to about 8.75 millimeters may be positioned in a triangular configuration at the corners 240 to maximize the exposed surface area for the adhesive 255. In other embodiments, the size and number of the apertures 235 in the corners 240 may be adjusted as necessary, depending on the chosen geometry of the corners 240, to maximize the exposed surface area of the adhesive 255. Further, the apertures 235 at the corners 240 may be fully housed within the third layer 215, substantially precluding fluid communication in a lateral direction exterior to the corners 240. The apertures 235 at the corners 240 being fully housed within the third layer 215 may substantially preclude fluid communication of the adhesive 255 exterior to the corners 240, and may provide improved handling of the dressing 104 during deployment at a tissue site. Further, the exterior of the corners 240 being substantially free of the adhesive 255 may increase the flexibility of the corners 240 to enhance comfort.

In some embodiments, the bond strength of the adhesive 255 may vary in different locations of the dressing 104. For example, the adhesive 255 may have a lower bond strength in locations adjacent to the third layer 215 where the apertures 235 are relatively larger, and may have a higher bond strength where the apertures 235 are smaller. Adhesive 255 with lower bond strength in combination with larger apertures 235 may provide a bond comparable to adhesive 255 with higher bond strength in locations having smaller apertures 235.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the third layer 215 to enhance the movement and proliferation of epithelial cells at a tissue site and reduce the likelihood of granulation tissue in-growth.

Further, the dressing 104 may permit re-application or re-positioning to reduce or eliminate leaks, which can be caused by creases and other discontinuities in the dressing 104 and a tissue site. The ability to rectify leaks may increase the reliability of the therapy and reduce power consumption in some embodiments. Thus, the dressing 104 in the example of FIG. 2 can provide a sealed therapeutic environment proximate to a tissue site, substantially isolated from the external environment, and the negative-pressure source 102 can reduce the pressure in the sealed therapeutic environment.

If not already configured, the dressing interface 270 may disposed over the aperture 275 and attached to the cover 116. The fluid conductor 265 may be fluidly coupled to the dressing interface 270 and to the negative-pressure source 102.

Negative pressure applied through the tissue interface 114 can create a negative pressure differential across the fluid restrictions 220 in the second layer 210, which can open or expand the fluid restrictions 220 from their resting state. For example, in some embodiments in which the fluid restrictions 220 may comprise substantially closed fenestrations through the second layer 210, a pressure gradient across the fenestrations can strain the adjacent material of the second layer 210 and increase the dimensions of the fenestrations to allow liquid movement through them, similar to the operation of a duckbill valve. Opening the fluid restrictions 220 can allow exudate and other liquid movement through the fluid restrictions 220 into the first layer 205 and the container 106. Changes in pressure can also cause the first layer 205 to expand and contract, and the interior border 250 of the third layer 215 may protect the epidermis from irritation. The second layer 210 and the third layer 215 can also substantially reduce or prevent exposure of tissue to the first layer 205 in order to inhibit growth of tissue into the first layer 205.

In some embodiments, the first layer 205 may be hydrophobic to minimize retention or storage of liquid in the dressing 104. In other embodiments, the first layer 205 may be hydrophilic. In an example in which the first layer 205 may be hydrophilic, the first layer 205 may also wick fluid away from a tissue site, while continuing to distribute negative pressure to the tissue site. The wicking properties of the first layer 205 may draw fluid away from a tissue site by capillary flow or other wicking mechanisms, for example. An example of a hydrophilic first layer 205 is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

If the negative-pressure source 102 is removed or turned-off, the pressure differential across the fluid restrictions 220 can dissipate, allowing the fluid restrictions 220 to move to their resting state and reduce the rate at which or prevent exudate or other liquid from returning to the tissue site through the second layer 210.

In some applications, a filler may also be disposed between a tissue site and the third layer 215. For example, if the tissue site is a surface wound, a wound filler may be applied interior to the periwound, and the third layer 215 may be disposed over the periwound and the wound filler. In some embodiments, the filler may be a manifold, such as an open-cell foam. The filler may comprise or consist essentially of the same material as the first layer 205 in some embodiments.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the second layer 210, which can open or expand the fluid restrictions 220 from their resting state to allow the instillation solution or other fluid to be distributed to the tissue site.

Figure 6:
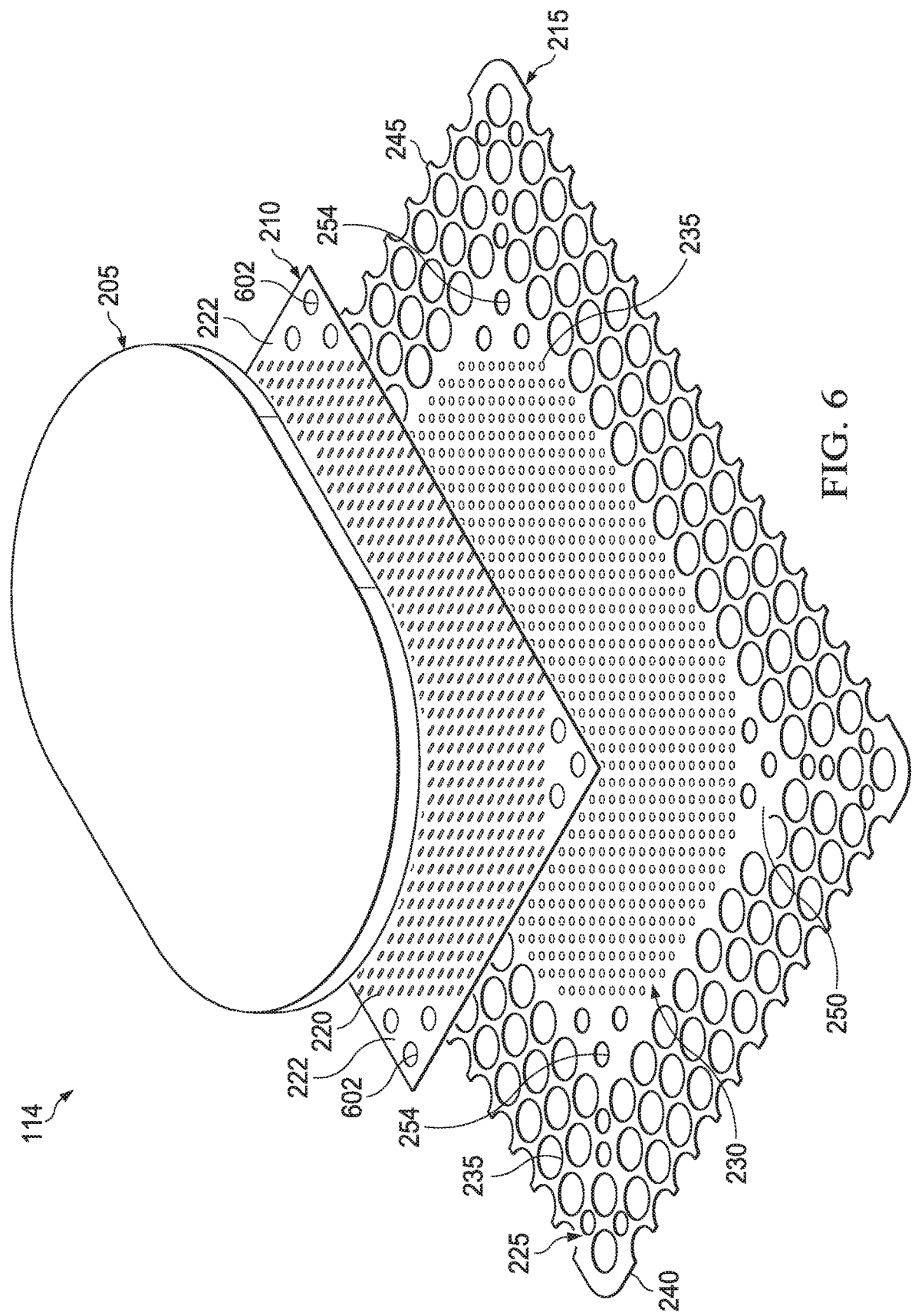
FIG. 6 is an assembly view of a tissue interface that may be associated with some additional embodiments of a dressing for use with the therapy system of FIG. 1.

FIG. 6 is an assembly view of another example of the tissue interface 114 of FIG. 1, illustrating additional details that may be associated with some embodiments. In some embodiments, the alignment areas 222 may be internal to the second layer 210 and do not protrude from an edge of the second layer 210. For example, as shown in FIG. 6, the second layer 210 may be rectangular in shape and may include alignment areas 222 in each of its four corners. The alignment areas 222 of the second layer 210 of FIG. 6 may each include one or more registration apertures, such as alignment apertures 602. The alignment apertures 602 may be configured so that when the second layer 210 is placed against the third layer 215, the alignment apertures 602 may be aligned with, or in some case be coextensive with one or more registration apertures, such as alignment holes 254, of the third layer 215.

Figure 7:
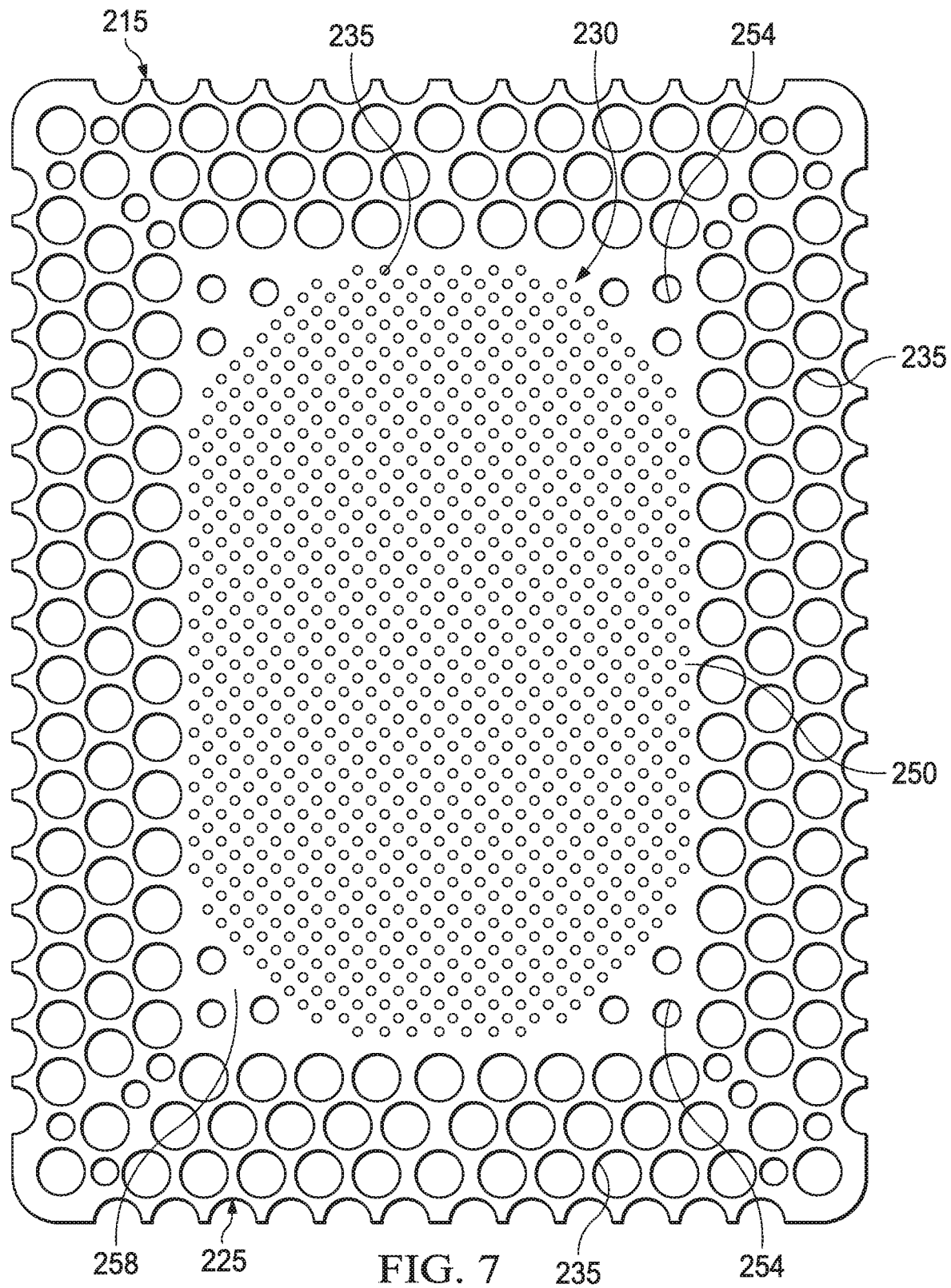
FIG. 7 is a schematic view of an example layer of the tissue interface of FIG. 6, illustrating additional details that may be associated with some embodiments.

Referring now also to FIG. 7, a schematic view of an example of the third layer 215, for use with the tissue interface 114 of FIG. 6, is shown, illustrating additional details that may be associated with some embodiments. The third layer 215 of FIG. 7 may include alignment holes 254, which may be configured to be aligned with the alignment apertures 602 of the second layer 210 of FIG. 6 during manufacture or assembly of the tissue interface 114 of FIG. 6. The alignment holes 254 of FIG. 7 may be positioned in one or more alignment regions 258 of the interior border 250 of the third layer 215, which may otherwise be substantially free of apertures, such as the apertures 235. As shown in FIG. 7, each of the four alignment regions 258 of the interior border 250 may include one or more alignment holes 254. In some instances, each of the four alignment regions 258 of the interior border 250 may include alignment holes 254 in the form of a group of three holes. For example, each of the alignment regions 258 may include alignment holes 254 comprising two or three holes measuring between 3 mm and 9 mm in diameter, for example, 6 mm in diameter. The alignment holes 254 may be arranged so that each hole of the group of three holes may be evenly spaced to span around the corner of the alignment region 258 of the interior border 250. For example, each of the alignment holes 254 may be spaced apart from the adjacent alignment hole 254 by a distance of between approximately 4 mm and 7 mm. In some alternative embodiments, a larger aperture 235 positioned in or adjacent to one or more of the alignment regions 258, such as an aperture 235 having a diameter between 8 mm and 12 mm, or in some instances 10 mm, may be used instead of the alignment holes 254 for alignment with the second layer 210.

Figure 8:
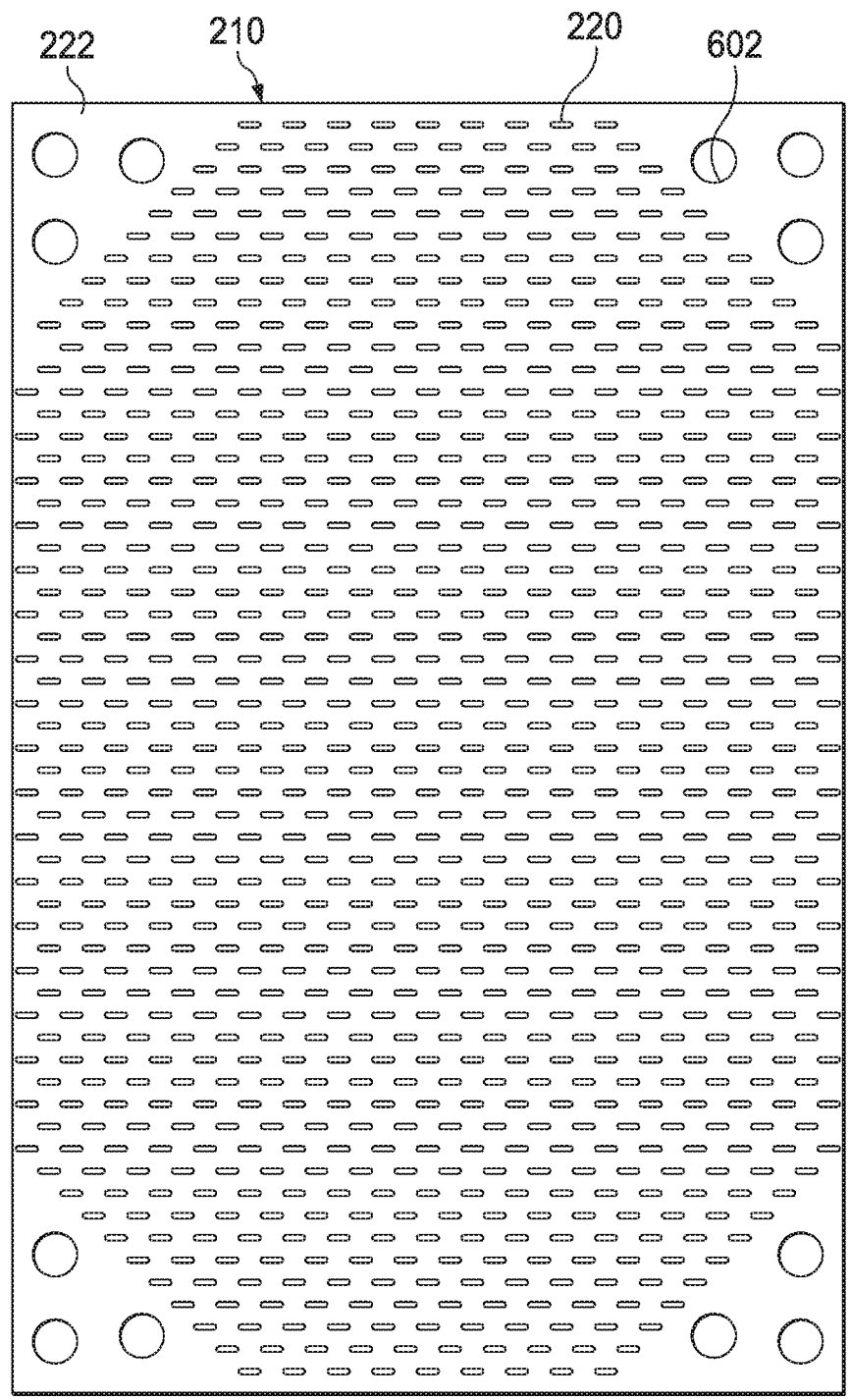
FIG. 8 is a schematic view of an example of another layer of the tissue interface of FIG. 6, illustrating additional details that may be associated with some embodiments.

FIG. 8 is a schematic view of the second layer 210 of FIG. 6, illustrating additional details that may be associated with some illustrative embodiments. The alignment areas 222 of FIG. 8 may be located or positioned in each of the four corners of the second layer 210. The alignment areas 222 of the second layer 210 may include alignment apertures 602 and may facilitate alignment with aspects of the third layer 215 of FIG. 7. As shown in FIG. 8, each of the three alignment apertures 602 in each of the alignment areas 222 may be approximately 6 mm in diameter and may be separated from each other by approximately 6 mm. However, other sizes, spacing distances, as well as shapes of the alignment apertures 602 may also be possible. For example, the alignment apertures 602 may be circular and measure between approximately 3 mm and 12 mm in diameter. In some embodiments, a spacing distance of between 4 mm and 8 mm between adjacent alignment apertures 602 may be used.

Figure 9:
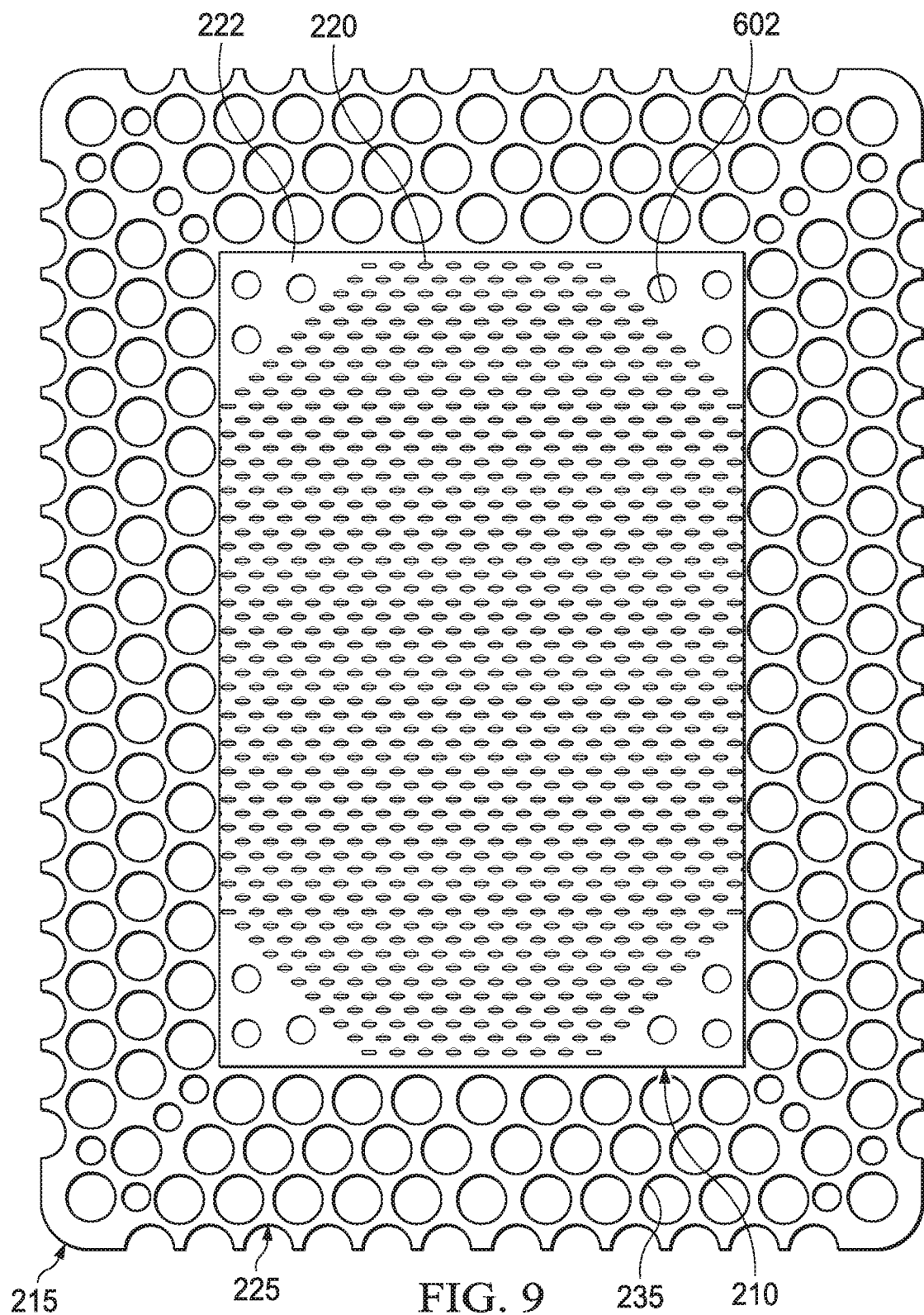
FIG. 9 is a schematic view of the example layer of FIG. 8 overlaid on the example layer of FIG. 7.

FIG. 9 is a schematic view of the second layer 210 of FIG. 8 overlaid on the third layer 215 of FIG. 7, illustrating additional details that may be associated with some example embodiments of the tissue interface 114. For example, as illustrated in FIG. 9, the fluid restrictions 220 may be aligned, overlapping, in registration with, or otherwise fluidly coupled to apertures 235 of the third layer 215. In some embodiments, one or more of the fluid restrictions 220 may be registered with the apertures 235 only in the interior portion 230 of the third layer 215, or only partially registered with the apertures 235. The fluid restrictions 220 in the example of FIG. 9 are generally configured so that each of the fluid restrictions 220 is registered with only one of the apertures 235.

As also illustrated in the example of FIG. 9, when the second layer 210 is overlaid on the third layer 215, the alignment areas 222 of the second layer 210, including the alignment apertures 602 may be positioned over the alignment regions 258 of the third layer 215, which include the alignment holes 254. When the alignment areas 222 of the second layer 210 are aligned with the alignment regions 258 of the third layer 215, each of the three alignment apertures 602 may be aligned with one of the three alignment holes 254, and the alignment holes 254 of the third layer 215 may not be covered by the material of the second layer 210, but are covered by portions of the cover 116 once it is applied to the tissue interface 114. The alignment areas 222 may be sized and positioned on the second layer 210, and the second layer 210 may be sized and shaped overall, such that the alignment areas 222 may align with the alignment regions 258 of the third layer 215 when the second layer 210 is positioned adjacent the interior portion 230 of the third layer 215. When in such position, the alignment apertures 602 of the alignment areas 222 of the second layer 210 may align with the alignment holes 254 of the alignment regions 258 of the third layer 215. Accordingly, the sizing and spacing of the alignment apertures 602 of the second layer 210 of FIG. 8 may substantially match, or otherwise be compatible with, the alignment holes 254 of the third layer 215 of FIG. 7.

In some alternative embodiments, each of the alignment areas 222 of the second layer 210 may include a greater or lesser number of alignment apertures 602, and likewise, each of the alignment regions 258 of the third layer 215 may also include a greater or lesser number of alignment holes 254. In some examples, at least one of the alignment areas 222 of the second layer 210 has at least one alignment aperture 602 that aligns with at least one alignment hole 254 of at least one of the alignment regions 258 of the third layer 215 when the second layer 210 is overlaid in the proper position on the third layer 215. The second layer 210 and third layer 215 may be configured so that when the alignment areas 222 of the second layer 210 are aligned with the alignment regions 258 of the third layer 215, the majority of the fluid restrictions 220 are each in registration with or otherwise fluidly coupled to at least one of the apertures 235 of the third layer 215.

In use, the alignment holes 254 of the third layer 215 and the alignment apertures 602 of the second layer may both be used in conjunction with an assembly tool for properly positioning and aligning the second layer 210 and the third layer 215 during construction of the tissue interface 114. For example, the third layer 215 may be placed on or over a portion of an assembly tool that may include a number of rods or pins configured to extend upwards through the alignment holes 254 of the third layer 215. The second layer 210 may then be overlaid on the third layer 215 so that the rods or pins of the assembly tool may also extend upwards through the alignment apertures 602 of the second layer 210. In other words, the rods or pins of the assembly tool may be threaded through both the alignment holes 254 and the alignment apertures 602 of the third layer 215 and second layer 210, respectively.

Methods of manufacturing may accommodate the multiple designs and embodiments of the alignment features of the second layer 210 and third layer 215, and allow for reel-to-reel volume manufacturing of the tissue interface 114 and dressing 104, as may be customary in the art. According to at least one example method for automated manufacturing and assembly of the dressing 104, each of the second layer 210 and the third layer 215 may be produced such that the fluid restrictions 220 and apertures 235 are registered to inter-layer registration points, such as the alignment features of the second layer 210 and third layer 215. For instance, the fluid restrictions 220 and apertures 235 may be registered to the alignment areas 222 and/or alignment apertures 602 of the second layer 210 and/or the alignment holes 254 of the third layer 215. For example, the fluid restrictions 220 and apertures 235 should be registered to the alignment features of their respective layers, such as the second layer 210 and the third layer 215, such that when the alignment features of the second layer 210 and the third layer 215 are aligned, the fluid restrictions 220 and apertures 235 are also correctly aligned. The fluid restrictions 220 and apertures 235 should be registered to the registration points within a reasonable tolerance, for example with a range of about 0.2 mm to 6 mm.

Each of the layers may be held on a manufacturing web and/or a roll, according to practices familiar to one skilled in the art. The third layer 215, which may be positioned on a manufacturing web, may then be moved to an assembly station, where rods or pins of an assembly tool may be raised through the alignment holes 254 of the third layer 215. In some embodiments, the second layer 210 may then be selected by a carrier mechanism, such as a shaped, high-flow vacuum cup that is articulated by a robot or other means. The second layer 210 may then be moved by the carrier mechanism and positioned over the protruding rods or pins of the assembly tool. A camera-based system may be used to automatically adjust the location of the second layer 210 so that the appropriate features of the second layer 210, depending on the particular embodiment, align with the protruding rods or pins of the assembly tool.

Once properly positioned over the third layer 215 and assembly tool, the carrier mechanism may lower the second layer 210 into place. For example, in some embodiments of the second layer 210 having alignment areas 222 comprising wings, as shown in FIG. 4, the wings may each be lowered down between two of the rods or pins. In some embodiments of the second layer 210 having alignment areas 222 comprising alignment apertures 602, the second layer 210 may be lowered down so that the rods or pins of the assembly tool pass through the alignment apertures 602. The second layer 210 may then be affixed to the third layer 215 by the carrier mechanism of the robot, which may then be retracted to its starting position. The protruding rods or pins may also be withdrawn or lowered, and the assembly tool may move to a next assembly station on a manufacturing web, which may correspond to another sample of the third layer 215.

In some instances, the rods or pins of the assembly tool may include laser guides. For example, low-power lasers may be integrated into the rods or pins, or other portions of the assembly tool in order to detect a point of registration on one or more of the layers of the dressing 104, such as the second layer 210 or third layer 215 of the tissue interface 114. In some embodiments, a low-power laser may be integrated into a rod or pin of the assembly tool and may project a laser beam upwards from the rod or pin to detect an edge of either or both of the second layer 210 and the third layer 215 or one or more holes, such as the alignment apertures 602 of the second layer 210 and/or the alignment holes 254 of the third layer 215. Based on the identification of alignment features of the one or more layers of the tissue interface 114 by the laser guides, the assembly tool may be better directed to automatically position and align the one or more layers of the dressing 104. Such laser guidance features are typically very precise as well as accurate.

To complete the assembly of the tissue interface 114, the first layer 205, which may comprise foam, may be positioned atop the second layer 210 using an automated camera system to position the first layer 205 within the boundary of the large apertures 235 of the underlying third layer 215. A laser or other automated vision system, as known in the art, may be utilized. A cover 116 may then be placed over the other layers forming the tissue interface 114. For example, the cover 116 may be located on another manufacturing web that is brought into union with the assembled layers of the tissue interface 114 and positioned over the first layer 205 and second layer 210 and sealing with the border of the third layer 215. The dressing 104 may then be removed from the master manufacturing web, and additional components, such as the release liner 260, dressing interface 270, and/or fluid conductor 265 may be fitted to the dressing 104.

In some additional or alternative embodiments, additional or substitute features of the layers of the tissue interface 114 and dressing 104 may be incorporated. For example, the second layer 210 may comprise a colored or semi-colored film for aiding with optical alignment with the third layer 215. Although colored, the second layer 210 may remain substantially transparent. Additionally or alternatively, the second layer 210 may include visual alignment aids, such as cross-hairs, printed on the film of the second layer 210 for aiding with alignment of the second layer 210 with the third layer 215 or other components of the dressing 104. In some embodiments, as part of the manufacturing and assembly process, automated alignment systems may use the one or more types of visual indicia mentioned above to align the second layer 210 and the third layer 215, as well as other layers of the tissue interface 114. For example, a vision system may scan for and identify one or more of the visual indicia and then adjust motors or servos of an automated assembly tool to ensure that the visual indicia of the two or more layers of the tissue interface 114 are aligned. Such visualization systems that are known to one skilled in the art may be employed.

In some additional or alternative embodiments, the second layer 210 may include a border surrounding the area of the second layer 210 comprising the fluid restrictions 220. In this additional border, the second layer 210 may include a plurality of larger apertures, so that when the second layer 210 is overlaid on the third layer 215, the larger apertures of the additional border area of the second layer 210 may align with the apertures 235 of the periphery 225 of the third layer 215. Accordingly, any of these additional apertures of the second layer 210, in conjunction with a corresponding aperture 235 of the third layer 215, may be used to align the second layer 210 with the third layer 215. The second layer 210 may additionally or alternatively include holes or apertures to align with any of the apertures 235 or other features of the third layer 215. In such instances, rather than the adhesive 255 on the bottom surface of the cover 116 being bonded directly to the periphery 225 of the third layer 215, the cover 116 and adhesive 255 may be bonded to the additional border area of the second layer 210, which may in turn be bonded to the periphery 225 of the third layer 215. For example, a cover 116 comprising a polyurethane drape and an adhesive 255 comprising an acrylic adhesive may be bonded to the polyethylene border of the second layer 210, which may be bonded to the silicone material of the periphery 225 of the third layer 215. By including the additional border of the second layer 210, the overall size of the second layer 210 may be matched to the third layer 215, which may further simplify the assembly process of the tissue interface 114 since each of the second layer 210 and third layer 215 may be supplied on a roll and the layers may be assembled using a reel-to-reel approach. In such embodiments, the adhesive properties of the various layers of the dressing 104 may be modified or adjusted as necessary to ensure a sustained laminate structure of the different layers.

In some further embodiments, at least a portion of the periphery 225 of the third layer 215 may be coated with an adhesive that may facilitate removal of the dressing 104 from a tissue site. For example, one or more portions of the periphery 225 may be coated with a light-switchable adhesive that may be triggered by a range of photo-initiators to cross-link and thus become brittle. Accordingly, when exposed to a photo-initiator, the adhesive bond strength of the adhesive may drop, which may enable the dressing 104 to be removed from a tissue site with less force. The light-switchable adhesive may be tailored such that a range of wavelengths may trigger the drop in bond strength, for example light ranging from UVA to sunlight, as well as white light.

In yet some additional embodiments, the third layer 215 may be modified such that rather than including the periphery 225 formed from a silicone material and comprising apertures 235, the periphery 225 may instead be formed from a standard drape material, such as a polyurethane drape, and may not include apertures. In still further embodiments, the periphery 225 of the third layer 215 may be omitted altogether. For example, the area of the third layer 215 outside of the interior border 250 may be omitted.

Methods of treating a surface wound to promote healing and tissue granulation may include applying the dressing 104 to a surface wound and sealing the dressing 104 to epidermis adjacent to the surface wound. For example, the third layer 215 may be placed over the surface wound, covering at least a portion of the edge of the surface wound and a periwound adjacent to the surface wound. The cover may also be attached to epidermis around the third layer 215. The dressing 104 may be fluidly coupled to a negative-pressure source, such as the negative-pressure source 102. Negative pressure from the negative-pressure source may be applied to the dressing 104, opening the fluid restrictions 220. The fluid restrictions 220 can be closed by blocking, stopping, or reducing the negative pressure. The second layer 210 and the third layer 215 can substantially prevent exposure of tissue in the surface wound to the first layer 205, inhibiting growth of tissue into the first layer 205. The dressing 104 can also substantially prevent maceration of the periwound.

The systems, apparatuses, and methods described herein may provide significant advantages over prior dressings. For example, some embodiments of the dressing 104 provide a negative-pressure dressing that is simple to assemble and apply to a tissue site, reducing the time to apply and remove. In some embodiments, the layers of the dressing 104, such as the second layer 210 and third layer 215 may be configured with built-in guides for correctly aligning the second layer 210 and third layer 215 with each other within the dressing 104. The guide portions of the second layer 210 and third layer 215 may therefore provide the user with a more accurate way for ensuring correct alignment of the second layer 210 and third layer 215 that may be easier to consistently perform without the user having to rely primarily on eyesight for achieving the proper placement of the layers. The guide portions of the second layer 210 and third layer 215 may provide means for more quickly and accurately assembling and/or positioning on a surface wound the layers of the dressing 104. As a result, manual as well as automated methods of assembling the layers of the dressing 104 during manufacturing may also be reliably accelerated. Furthermore, the guide features of the second layer 210 and third layer 215 may be scaled up or down in size to correspond to larger or smaller sizes of the layers of the tissue interface 114.

The dressing 104 may provide many benefits to a tissue site, such as good manifolding, beneficial granulation, protection of the peripheral tissue from maceration, and a low-trauma and high-seal bond. These characteristics may be particularly advantageous for surface wounds having moderate depth and medium-to-high levels of exudate. Some embodiments of the dressing 104 may remain on the tissue site for at least 5 days, and some embodiments may remain for at least 7 days. Antimicrobial agents in the dressing 104 may extend the usable life of the dressing 104 by reducing or eliminating infection risks that may be associated with extended use, particularly use with infected or highly exuding wounds.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A method of assembling a composite dressing, the method comprising:
   providing an assembly station having a plurality of retaining pins;
   placing a first layer having a plurality of apertures on the assembly station;
   engaging the plurality of retaining pins with at least some of the apertures to retain the first layer in at least one plane;
   placing a second layer having a plurality of fluid restrictions on the assembly station, wherein the second layer comprises at least one alignment area;
   engaging the at least one alignment area with at least one of the plurality of retaining pins so that at least some of the fluid restrictions are centrally aligned with at least some of the apertures; and
   bonding the second layer to the first layer.

2. The method of claim 1, wherein:
   the first layer comprises a central area and a peripheral area;
   apertures in the peripheral area are larger than apertures in the central area; and
   engaging the plurality of retaining pins with at least some of the apertures comprises engaging the plurality of retaining pins with apertures in the peripheral area.

3. The method of claim 1, wherein the fluid restrictions comprise a plurality of slots, each of the slots having a length less than 4 millimeters and a width less than 2 millimeters.

4. The method of claim 1, wherein the fluid restrictions comprise a plurality of slots, each of the slots having a length in a range of 2 millimeters to 4 millimeters and a width in a range of 0.5 millimeters to 2 millimeters.

5. The method of claim 1, wherein:
the first layer comprises a central area and a peripheral area;
apertures in the peripheral area are larger than apertures in the central area;
the apertures in the central area have a diameter of about 2 millimeters;
engaging the plurality of retaining pins with at least some of the apertures comprises engaging the plurality of retaining pins with apertures in the peripheral area; and
the fluid restrictions comprise a plurality of slots, each of the slots having a length in a range of 2 millimeters to 4 millimeters and a width in a range of 0.5 millimeters to 2 millimeters.

6. The method of claim 1, wherein:
the assembly station has at least four retaining pins;
engaging the plurality of retaining pins with at least some of the apertures comprises inserting the retaining pins through at least some of the apertures;
the at least one alignment area comprises a plurality of appendages on the second layer; and
engaging the at least one alignment area with the retaining pins comprises positioning each of the plurality of appendages in contact with two of the retaining pins to retain the second layer in at least one plane.

7. The method of claim 1, wherein:
the assembly station has at least four retaining pins;
engaging the plurality of retaining pins with at least some of the apertures comprises inserting the retaining pins through at least some of the apertures;
the at least one alignment area comprises a plurality of appendages on the second layer; and
engaging the at least one alignment area with the retaining pins comprises positioning each of the plurality of appendages in contact with a solid area of the first layer and in contact with two of the retaining pins to retain the second layer in at least one plane.

8. The method of claim 1, wherein:
the assembly station has at least two retaining pins;
engaging the retaining pins with at least some of the apertures comprises inserting the retaining pins through at least some of the apertures;
the at least one alignment area comprises alignment apertures; and
engaging the at least one alignment area with the retaining pins comprises inserting at least two of the retaining pins through the alignment apertures.

9. The method of claim 1, wherein:
the first layer has a first registration aperture;
the second layer has a second registration aperture; and
placing the second layer on the assembly station comprises aligning the first registration aperture with the second registration aperture.

10. The method of claim 1, wherein the first layer comprises a gel.

11. The method of claim 1, wherein the second layer comprises a polymer film.

12. The method of claim 1, wherein:
the first layer comprises a gel; and
the second layer comprises a polymer film.

13. The method of claim 1, wherein:
the first layer comprises a silicone gel; and
the second layer comprises a polyethylene film.

14. The method of claim 1, wherein at least one of the plurality of retaining pins comprises a laser configured to detect a first feature of the first layer and a second feature of the second layer.

* * * * *